(12) United States Patent
Lin et al.

(10) Patent No.: US 7,141,154 B2
(45) Date of Patent: Nov. 28, 2006

(54) SINGLE-STAGE SEPARATION AND ESTERIFICATION OF CATION SALT CARBOXYLATES USING ELECTRODEIONIZATION

(75) Inventors: YuPo J. Lin, Naperville, IL (US); Michael Henry, Batavia, IL (US); Jamie Hestekin, Morton Grove, IL (US); Seth W. Snyder, Lincolnwood, IL (US); Edward J. St. Martin, Libertyville, IL (US)

(73) Assignee: UChicago Argonne LLC, Chicago, IL (US)

( * ) Notice: Subject to any disclaimer, the term of this patent is extended or adjusted under 35 U.S.C. 154(b) by 407 days.

(21) Appl. No.: 10/794,231

(22) Filed: Mar. 5, 2004

(65) Prior Publication Data
US 2005/0056547 A1 Mar. 17, 2005

Related U.S. Application Data

(60) Provisional application No. 60/452,700, filed on Mar. 6, 2003.

(51) Int. Cl.
*B01D 61/48* (2006.01)
*B01D 61/44* (2006.01)

(52) U.S. Cl. .................... 204/524; 204/530; 204/533; 204/536; 204/541; 204/632

(58) Field of Classification Search ................ 204/524, 204/530, 533, 536, 541, 632
See application file for complete search history.

(56) References Cited

U.S. PATENT DOCUMENTS 6,495,014 B1 * 12/2002 Datta et al. ................. 204/533
6,797,140 B1 * 9/2004 Lin et al. .................... 204/524

* cited by examiner

*Primary Examiner*—Arun S. Phasge
(74) *Attorney, Agent, or Firm*—Emrich & Dithmar LLC

(57) ABSTRACT

A method of and apparatus for continuously making an organic ester from a lower alcohol and an organic acid is disclosed. An organic acid or salt is introduced or produced in an electrode ionization (EDI) stack with a plurality of reaction chambers each formed from a porous solid ion exchange resin wafer interleaved between anion exchange membranes or an anion exchange membrane and a cation exchange membrane or an anion exchange membrane and a bipolar exchange membranes. At least some reaction chambers are esterification chambers and/or bioreactor chambers and/or chambers containing an organic acid or salt. A lower alcohol in the esterification chamber reacts with an anion to form an organic ester and water with at least some of the water splitting with the ions leaving the chamber to drive the reaction.

27 Claims, 8 Drawing Sheets

SINGLE-STAGE SEPARATION AND ESTERIFICATION OF CATION SALT CARBOXYLATES USING ELECTRODEIONIZATION

RELATED APPLICATIONS

This application, pursuant to 37 C.F.R. 1.78(c), claims priority based on U.S. provisional application Ser. No. 60/452,700 filed on Mar. 6, 2003.

CONTRACTUAL ORIGIN OF THE INVENTION

The United States Government has rights in this invention pursuant to Contract No. W-31-109-ENG-38 between the U.S. Department of Energy (DOE) and The University of Chicago representing Argonne National Laboratory.

BACKGROUND OF THE INVENTION

Electrodeionization (EDI) is best known as a desalting process for dilute aqueous streams. Its commercial application has been limited to the production of ultra-pure water mainly for semiconductor and pharmaceutical industries. EDI technology based on a fixed resin-wafer has been disclosed in U.S. Pat. No. 6,495,014, the entire disclosure of which is incorporated by reference. Further disclosures of related EDI technology are in U.S. patent application Ser. No. 10/213,721 filed Aug. 6, 2002 entitled "ELECTRODEIONIZATION METHOD" and U.S. patent application Ser. No. 10/702,798 filed Nov. 5, 2003 entitled "IMMOBILIZED BIOCATALYTIC ENZYMES IN ELECTRODEIONIZATION (EDI)", the entire disclosures of which are incorporated by reference. This technology was originally developed for desalting industrial dextrose streams but its use can be extended to the application of EDI in the fields of chemical production, separation, and purification.

Organic esters, such as ethyl lactate, are attractive substitutes for many traditional solvents that are generally considered to be toxic. For this description, ethyl lactate is used as an example of a class of organic acid esters that are derived from the reaction of small alcohols such as methyl, ethyl, propyl, butyl, etc. with organic acids such as acetic, lactic, propionic, 3-hydroxy-propionic, butyric, etc. Ethyl lactate is a biodegradable chemical that has equivalent or superior solvent properties compared to many petroleum-based solvents. It is manufactured by esterification, i.e., reaction of ethanol and lactic acid. Although lactic acid is produced by fermentation, the acid is neutralized to the lactate salt to prevent media acidification and inhibition of biocatalytic activity. Therefore, the lactate salt must be converted back to lactic acid and the acid must be recovered and purified before esterification. The salt conversion and subsequent acid recovery can be the highest cost in the entire ester process, and is the greatest economic barrier to increased ethyl lactate production and utilization.

Various methods have been implemented or proposed to convert the salt to lactic acid. The utility of these methods can be affected by the type of base that is used to neutralize the lactic acid. The conventional approach uses hydrated lime for neutralization to form calcium lactate salt. Following fermentation the broth is acidified with sulfuric acid, which produces calcium sulfate and lactic acid. Calcium sulfate, which is only slightly soluble, precipitates during the acidification step and is removed from the broth by filtration. Although simple, this approach requires the addition of acid and produces nearly one pound of waste calcium sulfate for every pound of lactic acid that is produced.

Another approach uses sodium hydroxide or bicarbonate as the base for neutralization and a double electrodialysis process to concentrate the sodium lactate salt by desalting electrodialysis (DSED) and to split the salt into sodium hydroxide and lactic acid by water-splitting electrodialysis (WSED); the sodium hydroxide can then be recycled back to the fermentor. This approach is somewhat more economical than the conventional process because the DSED and WSED processes purify the lactate, as well as convert and separate it from the broth, and produce much less chemical waste. The DSED and WSED systems and membranes, however, represent significant capital and operating costs.

Yet another approach, referred to as direct esterification, uses ammonium hydroxide to neutralize the acid in the fermentor, DSED to concentrate and purify the ammonium lactate salt, and a pervaporation-assisted reactor to "thermally crack" ammonia gas from the ammonium lactate and remove it from the broth and to simultaneously carry out the esterification reaction. The primary difficulty with this approach is that ammonia and ethyl lactate can react irreversibly to produce lactamide that has no significant value and substantially reduces the ethyl lactate yield.

SUMMARY OF THE INVENTION

Based on the EDI concept and its capability of in-situ acidification, a new process has been discovered that converts the EDI system into a solid-phase acid/base catalytic reactor for chemicals produced from acid/base catalytic reactions. The ion-exchange resin beads in the EDI act as solid-phase acid/base catalysts and the ionic reactants and/or products are separated, in-situ, from each other by the applied electric field. This invention, in part relates to using the catalytic EDI separative reactor (CEDISR) to produce an organic ester. The invention combines, in one particular aspect, the separation of charged cation salt carboxylate substrates with an acid/base catalyzed alcohol esterification reaction. The reactor utilizes a fixed resin-wafer and electrodeionization (EDI) technology to form a separative reactor that carries out the separation and reaction in a single stage process.

It is an important object of the present invention to provide a method and apparatus for a single step esterification in an EDI stack.

Another object of the present invention to provide a method of continuously making an organic ester from a lower alcohol and an organic acid, comprising, introducing an organic acid or an organic salt into and/or producing an organic acid or an organic salt in an electrodeionization (EDI) stack having an anode and a cathode and a plurality of reaction chambers each formed from a porous solid ion exchange resin wafer interleaved between anion exchange membranes or an anion exchange membrane and a cation exchange membrane or an anion exchange membrane and a bipolar exchange membrane, providing mechanism for establishing an electric potential between the EDI anode and cathode, wherein at least one reaction chamber are esterification chambers and/or bioreactor chambers and/or chambers containing an organic acid or salt, whereby an organic acid or organic salt present in the EDI stack disassociates into a cation and an anion with the anion migrating into an associated esterification chamber through an anion exchange membrane if required and reacting with a lower alcohol in the esterification chamber to form an organic ester and water with at least some of the water splitting into a portion and a hydroxyl anion with at least some of the hydroxyl anion migrating to an adjacent chamber, said migration of ions being facilitated by establishing an electric potential across the EDI anode and cathode.

A still further object of the present invention is to provide an apparatus for manufacturing an organic ester, comprising an electrodeionization (EDI) stack having an anode and a cathode and a plurality of reaction chambers each formed from a porous solid ion exchange resin wafer interleaved between anion exchange membranes or an anion exchange membrane and either a cation exchange membrane or a bipolar membrane, mechanism for establishing an electrical potential between said EDI anode and said cathode, at least some of said reaction chambers being esterification chambers or esterification chambers separated from an adjacent bioreactor chamber by an anion exchange membrane and/or an acid/base capture chamber, said bioreactor chambers each containing an ion exchange resin wafer capable of forming an organic acid or salt from an ionizable fluid flowing therein, said esterification chambers each containing an ion exchange resin capable of forming an organic ester and wafer from a lower alcohol and an anion of the organic acid or salt, a source of anions supplied directly to said esterification chambers or supplied from adjacent chambers, and a supply of lower alcohol to said esterification chambers, whereby when a potential is established across said EDI anode and cathode at least some hydroxyl anions in said esterification chambers from water splitting migrate across anion exchange membranes to adjacent chambers to drive the reaction to continuously produce an organic ester.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

DESCRIPTION OF THE PREFERRED EMBODIMENT

Figure 1:
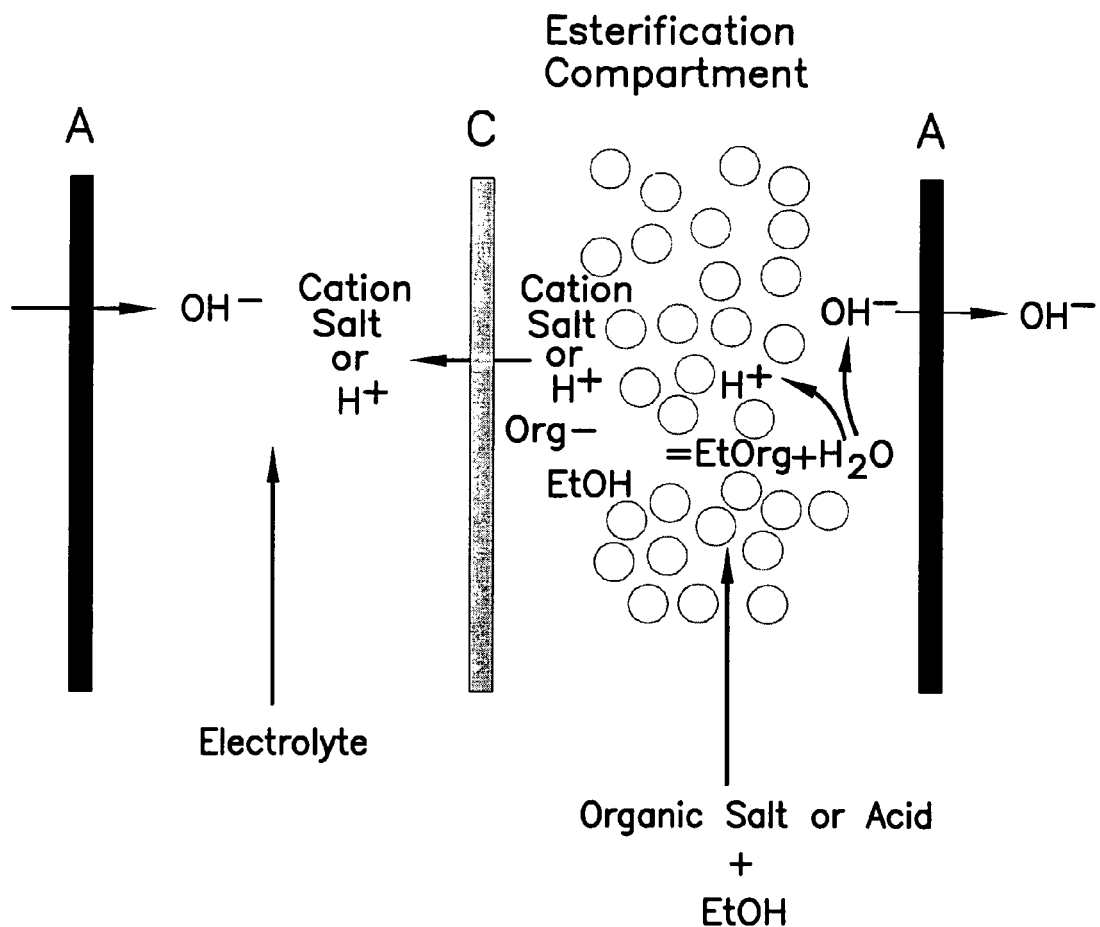
FIG. 1 is a schematic illustration of an acid/base catalytic esterification in reactor using an EDI stack.

A "single-stage esterification" that reacts the ethanol with the lactate salt to form ethyl lactate, therefore, provides both economic and process advantages. We used the CEDISR design to perform a single-stage esterification for organic ester production. The use of ion exchange resins to catalyze esterification has been reported in the literature, Walkup, Paul C. et. al., "*Production of Esters of Lactic Acid, Esters of Acrylic Acid, Lactic Acid and Acrylic Acid*", PCT/US91/00403, 1991. However, this invention is the first use of ion-exchange resin in an EDI configuration for simultaneous catalysis, from acid to ester form, and subsequent separation.

A "three-compartment" or three-chamber EDI configuration (see FIG. 2) is utilized to carry out the two-stage esterification. In the three-compartment EDI configuration, the fermentation broth, for example only containing lactate salt (e.g., sodium or ammonia lactate) or lactic acid and pure ethanol for example only are fed to the feed compartment and product compartment respectively. The counter cations (e.g., $Na^+$ or $NH_4^+$) are transported from the feed compartment to the base compartment or chamber. The lactate ions are transported to the product compartment or chamber that contains the cation and anion mixing resin wafer. These lactate ions react with ethanol to form ethyl lactate. Hereafter, chamber and compartment are used interchangeably and specific examples used are for purposes of illustration only and do not limit the invention.

The lactate ions are transported under the applied electric field from the feed chamber via the ion-exchange membrane to the reaction chamber and adsorb in the ion exchange resin. The ion exchange resin matrix provides the necessary conductive media for the lactate to move in the reaction chamber for esterification. Furthermore, esterification at the resin/liquid interface is enhanced by localized water splitting reaction of the ion exchange resins. The water in the reaction chamber is produced by the esterification reaction as well as leakage from experimental equipment. Water splitting (WS) is a well-known phenomenon in the EDI process that produces protons and hydroxyl ions moved due to the applied electric field. The hydroxyl ion from water splitting exchanges with the lactate ion adsorbed in the anion resin. Thus, the released lactate ion forms lactic acid with the proton from water splitting in the solution adjacent to the resin beads. The water splitting occurring either on the resin beads or on the surface of suitable ion-exchange membranes, such as a bipolar membrane, also provides excess protons to catalyze the esterification reaction. This electrical acidification is a major advantage and novel discovery in this process. The water produced from the esterification provides the water source for the water splitting reaction that produces an excess of protons (hydrogen ions) in the esterification chamber for catalyzing the further esterification as well as regenerating the cation resin. Consequently, increasing the water splitting rate by adjusting the applied current also accelerates the rate of ester production in the bulk fluid. (see FIG. 2) The excess hydroxyl ions produced by the water splitting are transported, via the anion resin, to the base compartment also known as an acid/base capture chamber, see FIG. 3. Therefore, in theory, no water accumulates in the product compartment and, thus, the hydrolysis of organic ester back to the starting, acid and alcohol is minimized or eliminated. This results in a high conversion yield of organic acid to organic ester.

The three-compartment EDI process eliminates the needed for purification and concentration of the lactic salt from the fermentation broth in conventional processes, which are energy intensive and significantly impact the overall cost of producing the product. With simple pre-filtration of the suspensions in the feed solution that is well known in the art, the fermentation broth can be directly fed into the three-compartment EDI for single-stage separation and esterification to produce organic ester, see FIG. 1. This invention reduces several processing steps from the traditional ester production scheme.

Figure 3:
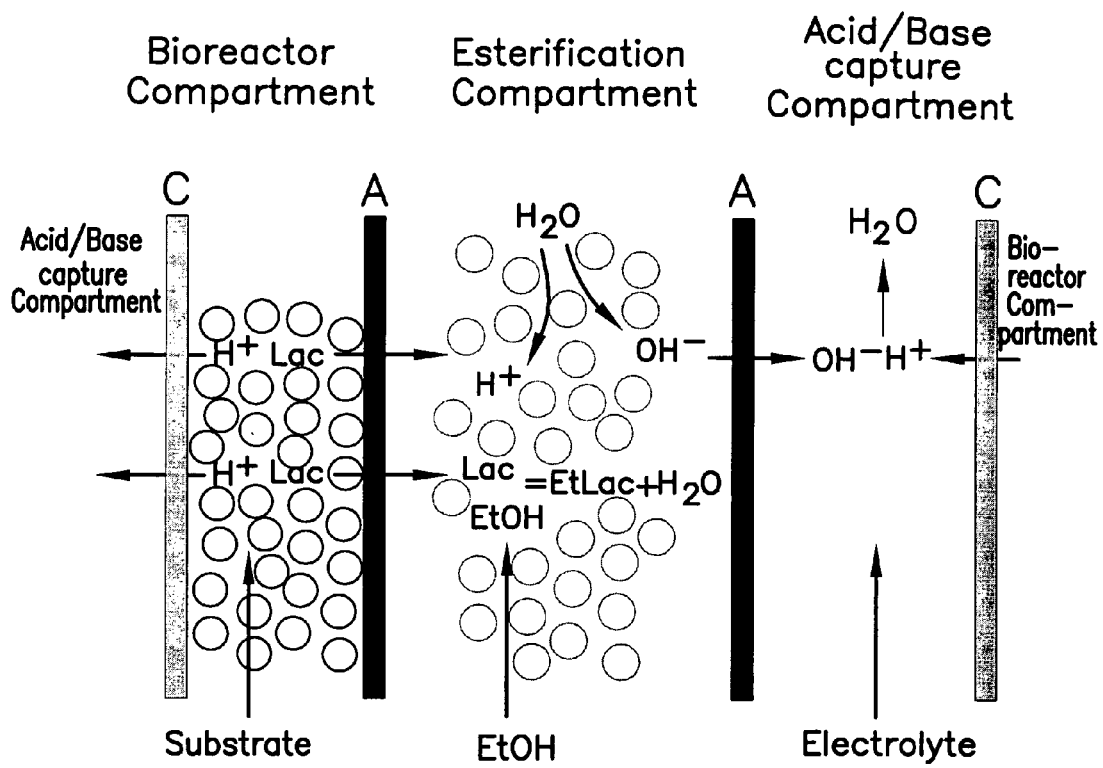
FIG. 3 is a schematic illustration of the combined separative bioreactor/catalytic reactor using three compartment EDI stack.

Another embodiment of the invention that further simplifies the process steps in producing the organic ester is to combine a EDI separative bioreactor (EDISB) with the CEDISR. In this process, either "three-compartment" or "two-compartment" EDI configurations are useful. FIG. 3 shows the configuration of the three-compartments EDI. As seen from the flow chart in FIG. 3, the esterification chamber is sandwiched by a substrate (bioreactor) chamber and an acid/base capture chamber. Both the substrate and esterification chambers have resin wafers therein, as described in the patent and patent applications referenced above and incorporated therein. The substrate compartment (bioreactor) is used to perform the biological reaction to produce the organic acid. The ionic organic salt is immediately transported as it is produced into the esterification compartment where pure ethanol is fed. At the same time, the proton in the bioreactor migrates or is will transported through a cation membrane into the acid/base capture compartment. Thus, the immediate removal of the produced organic acid benefits the biological reaction by avoiding the product inhibition as well as maintaining the optimal pH condition without buffers. The captured pure ionic organic in the esterification compartment performs esterification catalyzed by the cation resin. The water produced from the esterification is consumed to regenerate the ion exchange resin via the WS reaction. The hydroxyl ions generated from water splitting is transported through the anion-exchange membrane into the acid/base capture compartment and reacts with protons (i.e., traveling from the bioreactor compartment) to form water.

Figure 4:
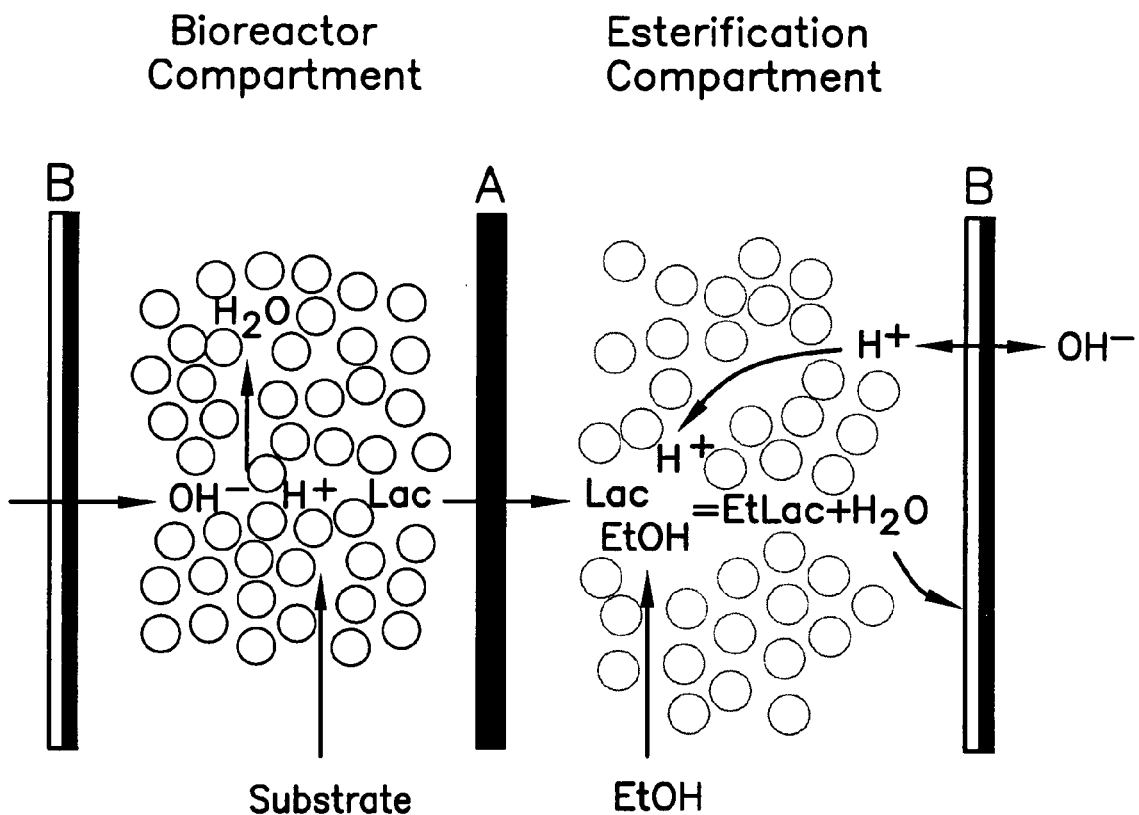
FIG. 4 is a schematic illustration of the combined separative bioreactor/catalytic reactor using two compartment EDI with a bipolar membrane.

The three-compartments combined separative biological/catalytic reactor (CSBCR) EDI can be converted into two-compartments EDI if it is needed. Using the esterification as the example, the acid/base capture compartment can be replaced by a bipolar ion-exchange membrane as shown in FIG. 4. Again, both two compartments have ion exchange resins therein. In this cell arrangement, the only ionic species forced to cross the ion-exchange membrane is the ionic organic salt generated in the substrate compartment (i.e., bioreactor). The proton in the substrate compartment is neutralized by the hydroxide ion generated on anion side of the bipolar membrane. The cation catalyst in the esterification compartment is regenerated by the proton produced by the cation side of bipolar membrane (i.e., via water splitting in the bipolar membrane). While both embodiments can be used as CSBCR, because of the hydrophilic property of bipolar membranes, the two-compartment EDI may cause more water to be transported into the catalytic rector compartment compared to the three-compartment design.

EXAMPLE 1

Figure 5:
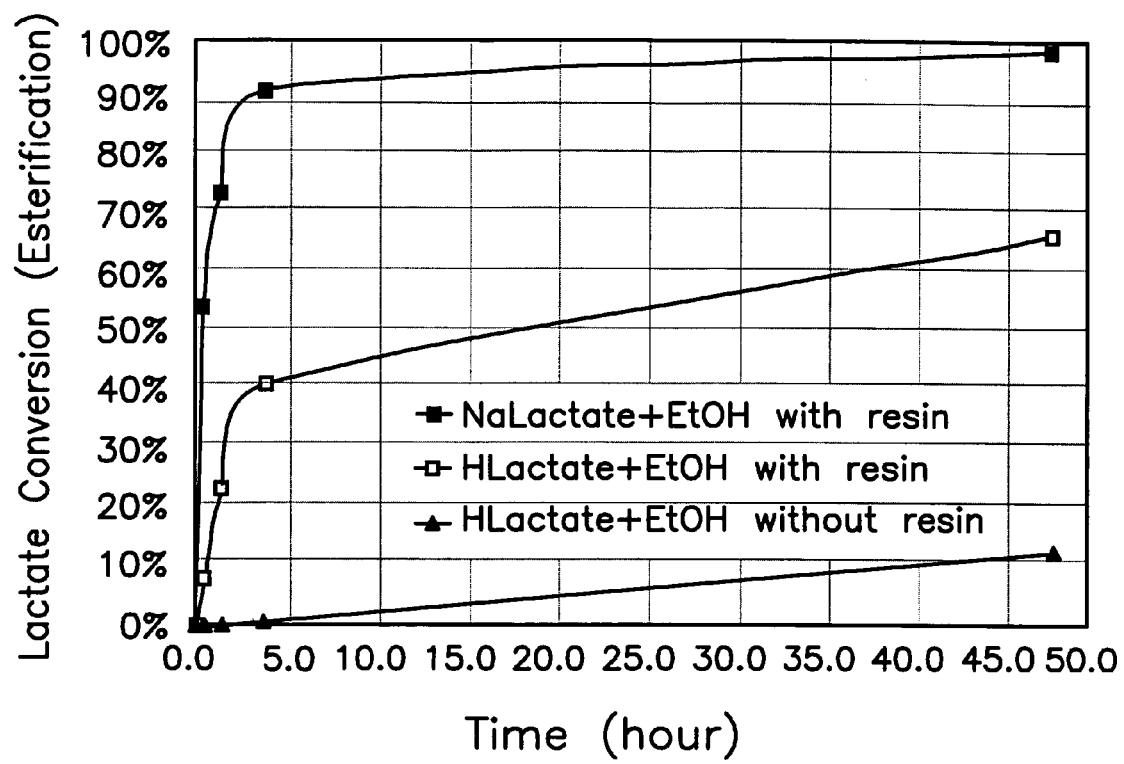
FIG. 5 is a graphical representation of the relationship between esterification and time for various conditions.

Three experiments are carried out to demonstrate the single-stage catalytic reactor of the esterification process, see FIG. 1. In the first two experiments, 1.35 mole percent of lactic acid or 0.83 mole percent of sodium lactate in ethanol with 2.5 g of cation-exchange resin ®DOWEX DR2030 (from Dow Chemical Inc.) are placed into two reactors respectively. The third experiment uses a reactor containing 1.35 mole percent of lactic acid in ethanol without the presence of a cation-exchange resin. The initial water content in the reactors is in the range of 3.5–3.6 mole percent. All the reactors are operated at 50° C. FIG. 5 shows the conversion of lactate to ester. Sodium lactate has a greater rate of conversion to the ester as compared with lactic acid in alcohol during the same period of operation. Sodium lactate which is more easily ionized to lactate ion shows more favorable esterification. The more limited amount of ionic lactate with the lactic acid solution appears to limit the esterification reaction. Without the addition of cation-exchange resins, the esterification reaction is two-orders of magnitude lower.

The results demonstrate that ionization of organic anion plays an important role in esterification. It also suggests that the use of EDI to extract the ionized organic anion and simultaneously perform esterification is a kinetically favorable process.

EXAMPLE 2

Figure 2:
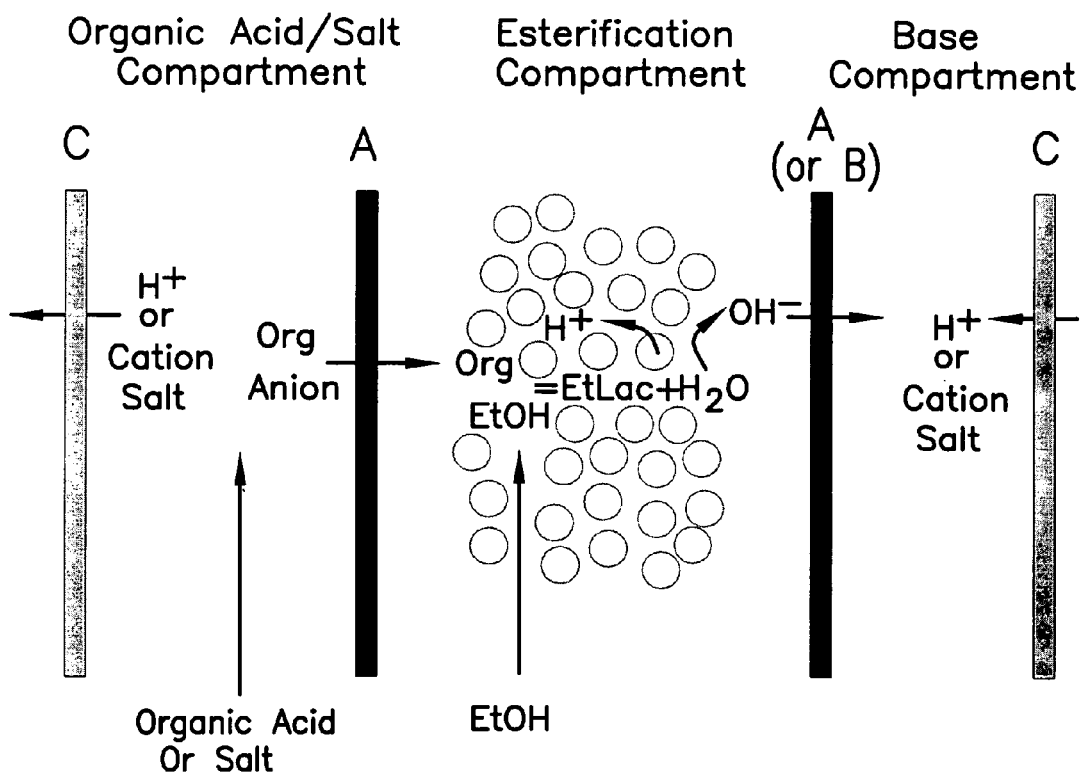
FIG. 2 is a schematic illustration of a two stage esterification process in an EDI stack.
Figure 6:
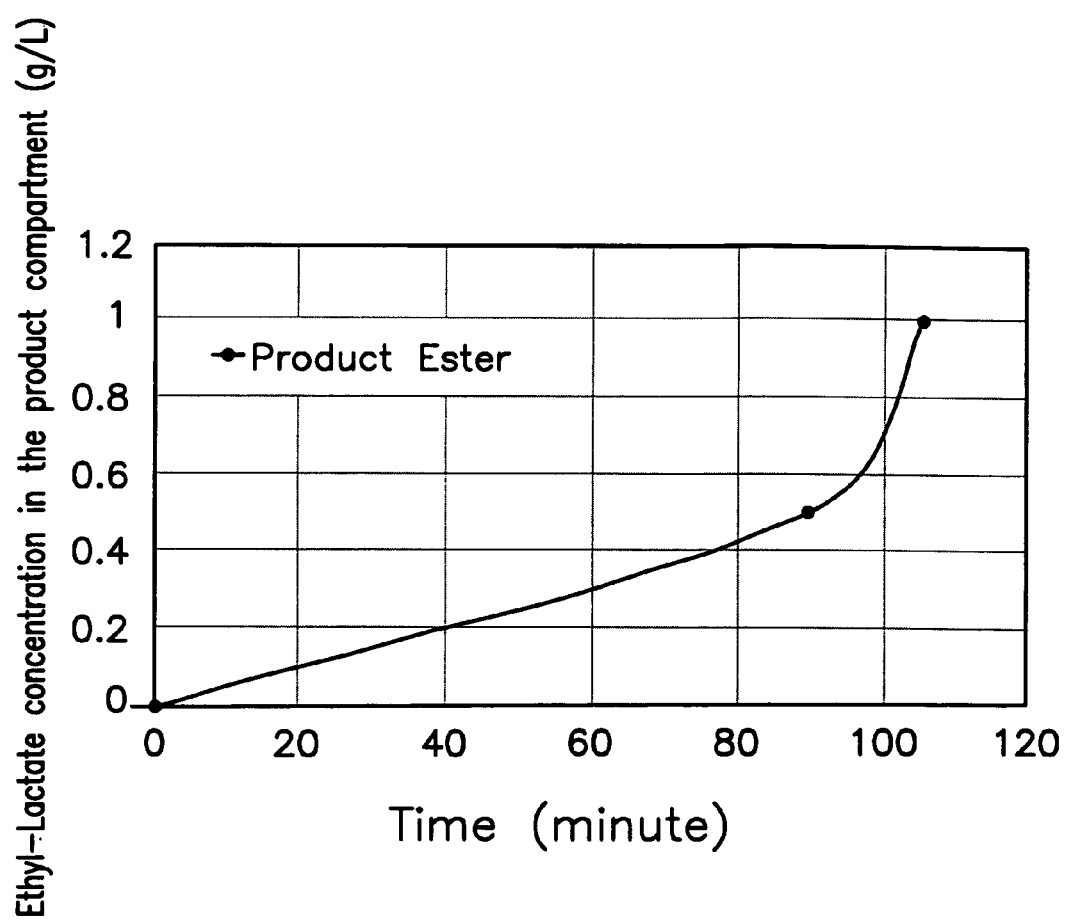
FIG. 6 is a graphical representation of the relationship between the concentration of ethyl lactate in the product as a function of time using a apparatus of the present invention.

Similar to the configuration showed in FIG. 2, a "three-compartment" EDI stack used to produce the ethyl lactate. An ED stack (Tokuyama Inc., model TS-2) filled with an immobilized resin wafer containing ®C100E (cation resin bead) and ®A444 (anion resin bead) ion-exchange resins (from Purolite Company) was used as the EDI device. ®AMH (anion permeable) and ®C6610F (cation permeable) ion exchange membranes (from Tokuyama Inc.) were used in the stack. The membrane surface area was 195 cm$^2$. A feed of 10% sodium lactate was re-circulated in the feed compartment (i.e., compartment 1 in FIG. 2). Pure ethanol was fed into the product compartment (compartment 2). Sodium hydroxide was recovered from the base compartment (compartment 3). The operating temperature was maintained around 35° C. FIG. 6 shows the production of ester obtained in the production compartment using this EDI stack. 4–6 wt. % of water was found in the product compartment which we attributed to diffusion through the membrane from the feed into the product compartment. The power consumption was around 0.1–0.2 kWh/lb of ethyl lactate produced. The power consumption for the single-stage EDI process is much lower than the estimated 1.1 kWh/lb and 0.9 kWh/lb of ethyl lactate produced, observed for production of ester using the double ED process and direct esterification process, respectively.

EXAMPLE 3

Figure 7:
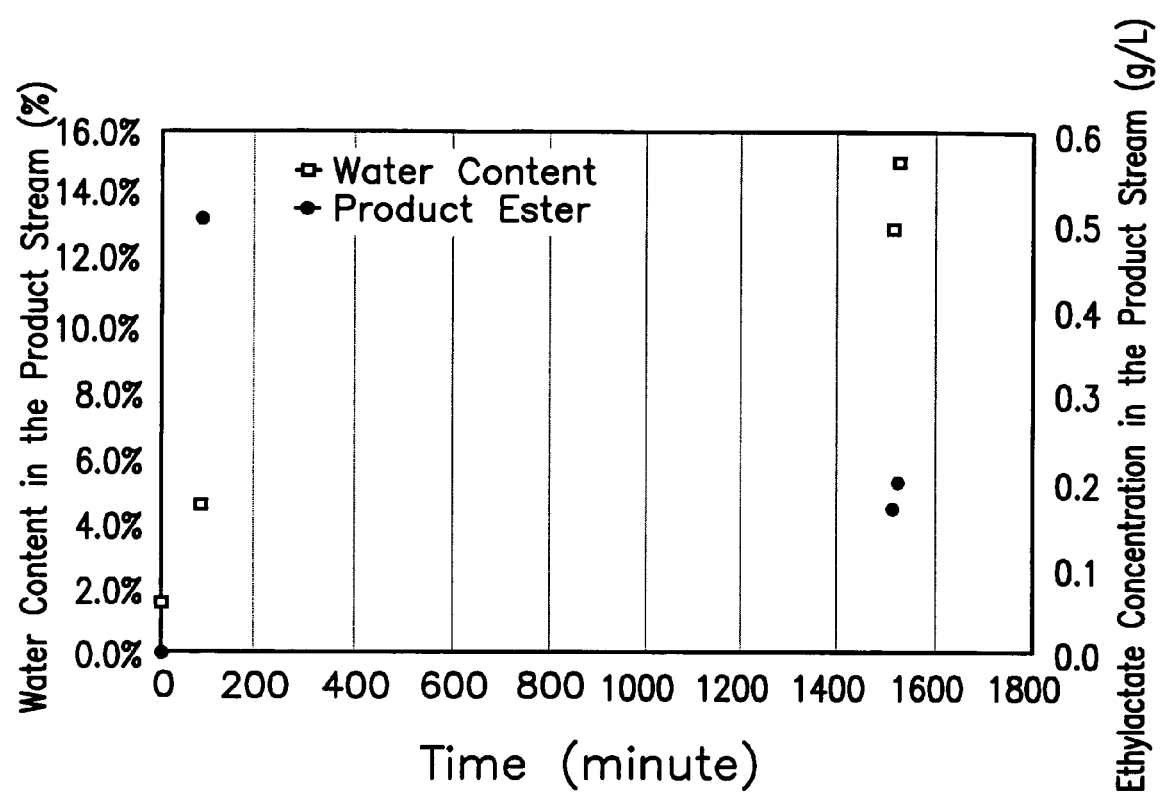
FIG. 7 is a graphical representation of the relationship between the water content in the product and the ester concentration in the product s a function of time for a two-chamber EDI set-up.

The same EDI stack as described in Example 2 was used, see FIG. 4. The ion-exchange membranes used in the stack were a bipolar membrane (®BP-1) and anion-exchange membrane (AMH) purchased from Tokuyama Inc. 1% sodium lactate was used to simulate the organic acid production in the substrate compartment. Pure ethanol was used in the esterification compartment. The operation temperature was maintained at 30° C. FIG. 7 shows the ester production and water content in the product. The high water content diffused from the substrate compartment eventually re-hydrated the ester after 1400 minutes operation.

EXAMPLE 4

Figure 8:
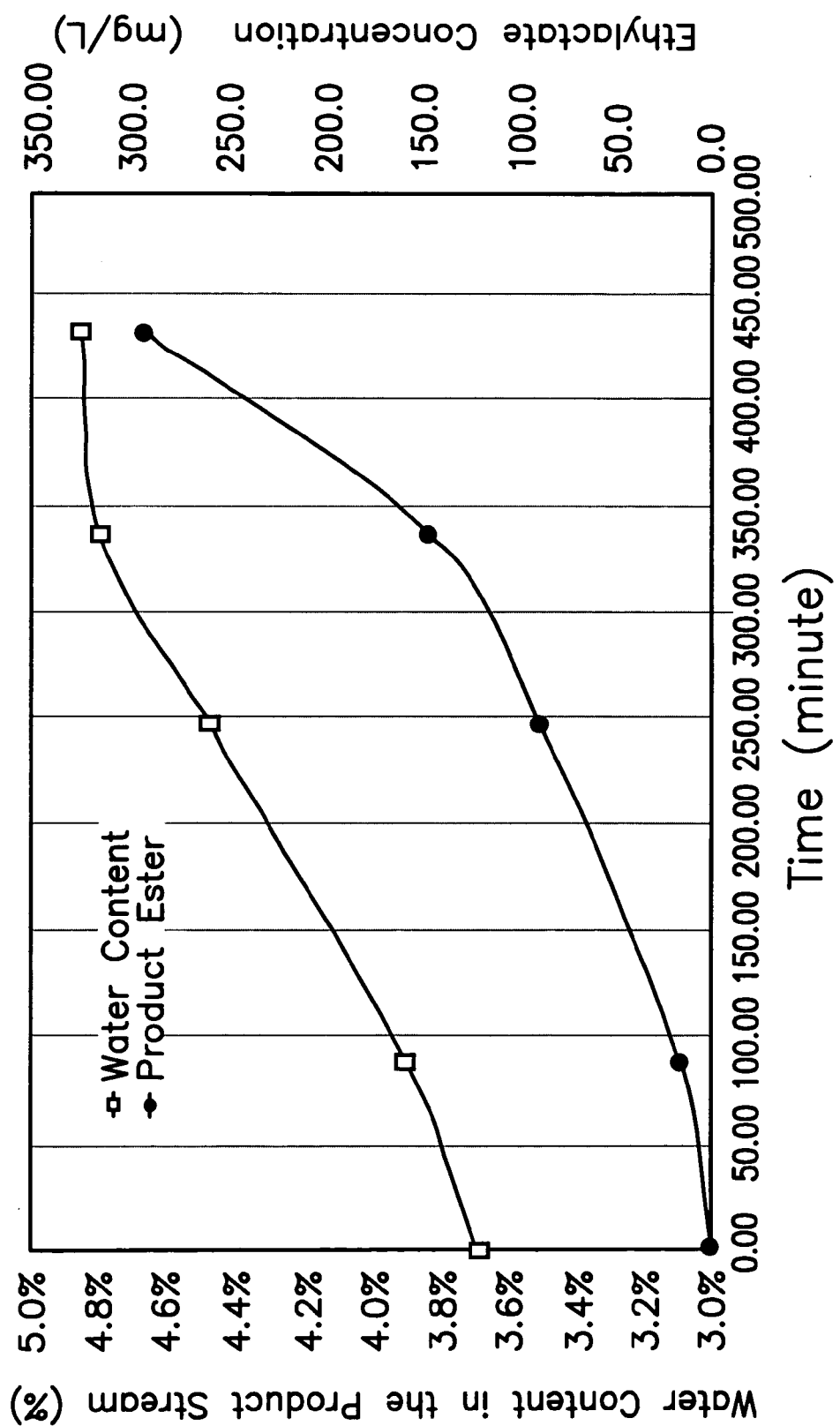
FIG. 8 is a graphical representation of the relationship between the water content in the product and the ester concentration in the product as a function of time for a three-chamber set-up.

In this Experiment, ®Amberlite 15 (from Rohm & Haas Inc.) cation exchange resin wafer was used in the esterification compartment. ®AMH (anion permeable) and ®C6610F (cation permeable) ion-exchange membranes were used in the EDI stack, as seen in FIG. 3. A mini-stack of electrodialysis (from ElectroCell AB Inc.) with 10 cm$^2$ membrane area was used. 1% sodium lactate was used to simulate the organic acid salt in the substrate compartment. The stack was operated about 25° C. FIG. 8 shows the water content and ester production. Table 1 lists the results of water, ethanol, lactate and ester in the esterification compartment. No re-hydration of ester was observed. The water in the product did not retard the esterification as was indicated by steadily increasing ester productivity and esterification conversion.

9 VOL. 126, No. 4, 994–995, 2004, used as co-solvents in the esterification compartment improves efficiency. Preferred electrolytes are one or more of 1-Hexyl-3-methyl-3H-imidazolium+tetrafluoro borate], [3-Methyl-1-octyl-3H-imidazolium+tetrafluoro borate], [Trihexyl-tetradecyl-phosphonium+tetrafluoro borate], [1-hexyl-2,3-dimethyl-3H-imidazolium+Trifluoro-methanesulfonate], but these are representative only.

The present invention has been described with respect to the production of ethyl lactate; however, the invention is not so limited. The invention pertains to the production of a wide variety of esters from lower alcohols and from organic acids. More particularly, the alcohols which may be used in the

TABLE 1

| Time Elapse (minute) | Current (A) | Product Ester (mg/L) | Product Water (g/L) | Product Lactate (mg/L) | Product Ethanol (g/L) | Esterification conversion (%) | Concentration equilibrium constant | Productivity Ester (mg/L/hour) | Water Content (wt. %) | Water Transport rate (g/L/hour) | Water Splitting (%) |
|---|---|---|---|---|---|---|---|---|---|---|---|
| 0.00 |  | 0.0 | 29.8 | 16.2 | 780 | 0 |  |  | 3.68% | 1.965 |  |
| 90.0 | 0.014 | 16.2 | 31.6 | 121.6 | 779 | 10 | 0.01 | 10.8 | 3.90% | 1.868 | 47.6 |
| 250.0 | 0.014 | 89.3 | 36.4 | 211.1 | 775 | 25 | 0.04 | 21.4 | 4.48% | 1.852 | 59.2 |
| 340.0 | 0.014 | 146.2 | 39.0 | 276.2 | 773 | 30 | 0.05 | 25.8 | 4.80% | 1.842 | 58.7 |
| 435.0 | 0.014 | 292.5 | 39.5 | 357.5 | 772 | 40 | 0.08 | 40.4 | 4.86% | 1.703 | 52.1 |

Diffusion of water through the ion-exchange membranes may limit the extent of the esterification reaction due to subsequent hydrolysis of the ester. An additional pervaporation operation of the product stream from the single-stage EDI device to extract the diffusion water in the product stream (i.e., the ethanol and ester) can be utilized to reduce the accumulation of water. Another embodiment is to use hydrophobic membranes to limit the amount of water that is transported across the membrane by diffusion. These commercially-available membranes also allow the system to operate at higher temperatures, which increase the rates of ion transport and esterification reaction and increase the solution conductivity, all of which are beneficial.

Water produced as a product of the esterification reaction can be removed by adjusting the stack current so as to maximize the removal of water from the esterification chamber by water splitting. Toward this, increasing resin wafer thickness improves distribution of water splitting along the length of the resin wafer. Good water splitting distribution is also important to continually regenerate the full length of the resin wafer.

The ratio of anion to cation exchange capacity in the wafer may also have a strong influence on the efficiency of the process. For example, wafers with a high cation to anion contact protons that have been adsorbed at a cation exchange site. Conversely, the reaction rate may be enhanced when protons in solution contact lactate anions that have been adsorbed on an anion exchange site.

Conductivity in the esterification plays important role in the inventive process. Pure alcohol has very low conductivity causing inefficient organic acid transport from the bioreactor compartment. A good supporting electrolyte, such as ionic liquids as reported by J. D. Holbrey, K. R. Seddon, "Ionic Liquids—review", Clean Product and Process, 1, 223–236, 1999; "Ionic Liquid as Green Solvent: Progess and Prospects", 24$^{th}$ American Chemical Society National Meeting, Boston, Mass., 2002; Walkup, Paul C. and et. al., "Production of Esters of Lactic Acid, Esters of Acrylic Acid, Masafumi Yoshio, Tomohiro Mukai, Hiroyuki Ohno, and Takashi Kato, "One-Dimensional Ion Transport in Self-Organized Columnar Ionic Liquids", J. AM. CHEM. SOC.

present invention include but are not limited to methyl, ethyl, propyl or butyl alcohol and may have alcohols up to 6 carbons in the alkyl chain. ethyl, propyl or butyl alcohol and may have alcohols up to 6 carbons in the alkyl chain. Although lactic acid has been used in the specific examples of the present invention, a wide variety of organic acids are applicable, most particularly carbocyclic acids. One or more of a mono, di, tri-carboxyclic acid group may be used and more specifically, acetic acid, lactic acid, propionic acid, 3-hydroxy-propionic acid, butyric acid or succinic acid may all be used in the present invention. Preferably, the reaction chamber containing the organic acid or salt in maintained at a pH in the range of from about 2 to about 7 and the pH in the esterification chamber is preferably maintained in the range of from about 2 to about 7. As previously described in the incorporated patent and patent applications identified above, the ion exchange resins are in the form of a flexible porous ion exchange material containing one or more of anion exchange entities or cation exchange entities or mixtures thereof immobilized with respect to each other with a binder comprising about 25% to about 45% by weight of ion exchange material without substantially coating the entities. In general, the porous ion exchange material contains a porosity somewhere in the range of from about 15% to about 60% and the binder is present preferably in an amount not greater than 80% of the entities. As before mentioned, the esterification chamber may be defined, as previously shown, by two anion exchange membranes or defined by an anion exchange membrane and a bipolar membrane or defined by an anion exchange membrane and a cation exchange membrane. In a combined separative bioreactor/catalytic reactor, each esterification chamber is adjacent a bioreactor chamber or a chamber containing either an organic acid or salt, with the esterification chambers bounded by an anion exchange membrane on one side and either an anion exchange membrane or a bipolar membrane on the other side. In the three chamber configuration, each esterification chamber is adjacent to one bioreactor chamber and an acid/base capture chamber.

While particular embodiments of the present invention have been shown and described, it will be appreciated by those skilled in the art that changes, modifications and improvements may be made, for example in the processing of the materials or in the electrode and/or cell design without departing from the true spirit and scope of the invention.

The embodiments of the invention in which an exclusive property or privilege is claimed are defined as follows:

1. A method of continuously making an organic ester from a lower alcohol and an organic acid, comprising, introducing an organic acid or an organic salt into and/or producing an organic acid or an organic salt in an electrodeionization (EDI) stack having an anode and a cathode and a plurality of reaction chambers each formed from a porous solid ion exchange resin wafer interleaved between anion exchange membranes or an anion exchange membrane and a cation exchange membrane or an anion exchange membrane and a bipolar exchange membrane, providing mechanism for establishing an electric potential between the EDI anode and cathode, wherein at least some reaction chambers are esterification chambers and/or bioreactor chambers and/or chambers containing an organic acid or salt, whereby an organic acid or organic salt present in the EDI stack disassociates into a cation and an anion with the anion migrating into an associated esterification chamber through an anion exchange membrane if required and reacting with a lower alcohol in the esterification chamber to form an organic ester and water with at least some of the water splitting into a proton and a hydroxyl anion with at least some of the hydroxyl anion migrating to an adjacent chamber, said migration of ions being facilitated by establishing an electric potential across the EDI anode and cathode.

2. The method of claim 1, wherein the organic acid is a carboxylic acid.

3. The method of claim 1, wherein the organic acid includes one or more of a mono-, di-, and tricarboxylic acid group.

4. The method of claim 1, wherein the organic acid is one or more of acetic, lactic, propionic, 3-hydroxyl-propionic, butyric, or succinic acid.

5. The method of claim 1, wherein the organic salt is a salt of one or more of acetic acid, lactic acid, propionic acid, 3-hydroxyl-propionic acid, butyric acid, or succinic acid.

6. The method of claim 1, wherein the alcohol has up to about 6 carbons in the alkyl chain.

7. The method of claim 1, wherein the alcohol is one or more of methyl, ethyl, propyl, or butyl.

8. The method of claim 1, wherein the pH in the reaction chamber containing the organic acid or salt thereof is maintained in the range of from about 2 to about 7.

9. The method of claim 1, wherein the pH in the esterification chamber is maintained in the range of from about 2 to about 7.

10. The method of claim 1, wherein the ion exchange resins are in the form of flexible porous ion-exchange material containing one or more of anion-exchange entities or cation-exchange entities or mixtures thereof immobilized with respect to each other with a binder comprising about 25% to about 45% by weight of the porous ion-exchange material without substantially coating the entities.

11. The method of claim 10, wherein the porous ion-exchange material contains at least 15% porosity and the binder is present in an amount not greater than 80% by weight of the entities.

12. The method of claim 11, wherein the porous ion-exchange material has a porosity in the range of from about 15% to about 60%.

13. The method of claim 1, wherein the ion-exchange material is one or more of a strong acid resin or a weak acid resin or a strong basic resin or a weak basic resin.

14. The method of claim 1, wherein the ester is a lactate, acetate, butyrate, propionate, 3-hydroxy propionate, or a succinate.

15. The method of claim 1, wherein the EDI stack has alternating bioreactor chambers for producing an organic acid and esterification chambers for producing organic esters by reacting an organic acid anion with an alcohol.

16. The method of claim 1, wherein the EDI stack has alternating esterification chambers and acid/base capture chambers.

17. The method of claim 1, wherein the EDI stack has a plurality of esterification chambers for producing organic esters by reacting an organic acid anion with an alcohol each esterification chamber located between a bioreactor chamber for producing an organic acid and an acid/base capture chamber for combining a cation from the adjacent bioreactor chamber and an anion from the adjacent esterification chamber.

18. The method of claim 1, wherein water splitting occurs either in the esterification chambers and/or at the bipolar membranes with the proton taking part in the esterification reaction and the hydroxyl anion migrating into the adjacent bioreactor chamber.

19. The method of claim 1, wherein an electrolyte is present in the esterification chambers.

20. The method of claim 19, wherein the electrolyte is one or more of 1-Hexyl-3-methyl-3H-imidazolium+tetrafluoro borate, 3-Methyl-1-octyl-3H-imidazolium+tetrafluoro borate, Trihexyl-tetradecyl-phosphonium+tetrafluoro borate, 1-hexyl-2,3-dimethyl-3H-imidazolium+Trifluoro-methanesulfonate.

21. An apparatus for manufacturing an organic ester, comprising an electrodeionization (EDI) stack having an anode and a cathode and a plurality of reaction chambers each formed from a porous solid ion exchange resin wafer interleaved between anion exchange membranes or an anion exchange membrane and either a cation exchange membrane or a bipolar membrane, mechanism for establishing an electrical potential between said EDI anode and said cathode, at least some of said reaction chambers being esterification chambers or esterification chambers separated from an adjacent bioreactor chamber by an anion exchange membrane and/or an acid/base capture chamber, said bioreactor chambers each containing an ion exchange resin wafer capable of forming an organic acid or salt from an ionizable fluid flowing therein, said esterification chambers each containing an ion exchange resin wafer capable of forming an organic ester and water from a lower alcohol and an anion of an organic acid or salt, a source of anions supplied directly to said esterification chambers or supplied from adjacent chambers, and a supply of lower alcohol to said esterification chambers, whereby when a potential is established across said EDI anode and cathode at least some hydroxyl anions in said esterification chambers from water splitting migrate across said anion exchange membranes to adjacent chambers to drive the reaction to continuously produce an organic ester.

22. The apparatus of claim 21, wherein each esterification chamber is defined by two anion exchange membranes.

23. The apparatus of claim 21, wherein each esterification chamber is defined by an anion exchange membrane and a bipolar membrane.

24. The apparatus of claim 21, wherein each esterification chamber is defined by an anion and a cation exchange membrane.

25. The apparatus of claim 21, wherein each esterification chamber is adjacent a bioreactor chamber.

26. The apparatus of claim 21, wherein each esterification chamber is adjacent one bioreactor chamber and an acid/base capture chamber.

27. The apparatus of claim 21, wherein an electrolyte is transferred from a source thereof to said esterification chambers.

* * * * *